United States Patent
Gupta et al.

(10) Patent No.: US 8,679,557 B2
(45) Date of Patent: Mar. 25, 2014

(54) SYNERGISTIC HERBAL OPHTHALMIC FORMULATION FOR LOWERING THE INTRA OCULAR PRESSURE IN CASE OF GLAUCOMA

(75) Inventors: Suresh Kumar Gupta, New Delhi (IN); Shyam Sunder Agrawal, New Delhi (IN); Renu Agrawal, New Delhi (IN); Sushma Srivastava, New Delhi (IN); Ankita Nagpal, New Delhi (IN); Naresh Kumar, New Delhi (IN); Rohit Saxena, New Delhi (IN); Sateesh Kumar Chauhan, New Delhi (IN); Deepak Bahri, New Delhi (IN)

(73) Assignees: Sentiss Pharma Private Limited, New Delhi (IN); Delhi Institute of Pharmaceutical Sciences and Research (DIPSAR), New Delhi (IN)

( * ) Notice: Subject to any disclaimer, the term of this patent is extended or adjusted under 35 U.S.C. 154(b) by 627 days.

(21) Appl. No.: 12/529,015

(22) PCT Filed: Feb. 27, 2008

(86) PCT No.: PCT/IB2008/000419
§ 371 (c)(1),
(2), (4) Date: Nov. 3, 2009

(87) PCT Pub. No.: WO2008/104856
PCT Pub. Date: Sep. 4, 2008

(65) Prior Publication Data
US 2010/0112106 A1    May 6, 2010

(30) Foreign Application Priority Data

Feb. 27, 2007 (IN) .............................. 431/DEL/2007

(51) Int. Cl.
*A61K 36/906* (2006.01)
*A61K 36/00* (2006.01)

(52) U.S. Cl.
USPC .......................................... 424/756; 424/725

(58) Field of Classification Search
None
See application file for complete search history.

(56) References Cited

U.S. PATENT DOCUMENTS 5,538,974 A * 7/1996 Ogawa et al. ............ 514/252.13

FOREIGN PATENT DOCUMENTS

WO          WO 03080091          * 10/2003          ............. A61K 35/78

OTHER PUBLICATIONS

Ross et al. Medicinal Plants of the World: Chemical Constituents, Traditional and Modern Medicinal Uses. Humana Press. 2003. p. 235.*
Godkar et al. Hypocholesterolemic effect of turmeric extract on Swiss mice. Indian Journal of Pharmacology. 1996. vol. 28. No. 3. pp. 171-174.*
Park et al. Absorption of intestinal free cholesterol is lowered by supplementation of *Areca catechu* L. extract in rats. Life Sciences. 2002. 70. pp. 1839-1859.*
Lee et al. 150kDa glycoprotein isolated from *Solanum nigrum* Linne enhances activities of detoxicant enzymes and lowers plasma cholesterol in mouse. Pharmacological Research. 51 (2005). 399-408.*
Amrani et al. Hypolipadaemic activity of aqueous *Ocimum basilicum* extract in acute hyperlipadaemia induced by triton WR 1339 in rats and its antioxidant property. Phytotherapy Research. 20. 1040-10745. 2006. pp. 1040-1045.*

* cited by examiner

*Primary Examiner* — Chris R Tate
(74) *Attorney, Agent, or Firm* — Birch, Stewart, Kolasch & Birch, LLP

(57) ABSTRACT

The present invention relates to a synergistic herbal composition for lowering the intra ocular pressure in different types of glaucoma and process for the preparation of the same in pharmaceutically acceptable dosage forms.

17 Claims, No Drawings

SYNERGISTIC HERBAL OPHTHALMIC FORMULATION FOR LOWERING THE INTRA OCULAR PRESSURE IN CASE OF GLAUCOMA

FIELD OF THE INVENTION

The present invention relates to a synergistic herbal composition for lowering the intra ocular pressure in different types of glaucoma and process for the preparation of the same in pharmaceutically acceptable dosage forms.

BACKGROUND OF THE INVENTION

Glaucoma is a disease characterized by high intraocular pressure (IOP) sufficient to cause either temporary or permanent impairment of vision. The rise in IOP might be due to:
  Increased rate of aqueous formation
  Decreased rate of out flow
  Raised pressure in the draining episcleral veins.

An obstruction to the circulation of the aqueous at the pupil or to its drainage through the angle of the anterior chamber causes glaucoma. The normal IOP of an individual ranges up to 20 mm Hg and can rise up to 60 to 70 mm of Hg in glaucoma patients. Raised IOP of this magnitude can result in loss of vision by causing damage to retinal nerve fibers. Optic nerve axons of the eyeball become compressed at the optic disc due to elevated IOP. This compression probably blocks the axonal flow of cytoplasm from the neuronal cell bodies in the retina to the extended optic nerve fibers entering the brain. It results in lack of nutrition of fibers and ultimately causes death of the neurons. Compression of retinal artery may increase the neuronal damage due to reduction in retinal nutrition.

Glaucoma is Generally Classified as
  Primary
  Developmental
  Secondary

The commonest form of glaucoma is primary glaucoma; it can be:

Open Angle Glaucoma:
  Angle of the anterior chamber is always open, at all stages of disease, and aqueous has access to the outflow channels at all times. There is increased resistance to outflow in the corneoscleral meshwork. IOP may be raised or elevated.

Angle Closure Glaucoma:
  No abnormal resistance to outflow in the corneoscleral meshwork is observed. The sole cause of elevated tension is closure of the angle. The iris obstructs the access of aqueous humor to the outflow channels.

Magnitude of the Disease
  Glaucoma is the third major cause of avoidable blindness. The global estimate of blindness is over 44 million with glaucoma accounting for more than 15% of the blind patients worldwide (2). Worldwide approximately two-thirds of all blind or visually impaired people are women (3). India has a high burden of blind (23.5%) in the world and 13% of the global blindness due to glaucoma is in India. Many population-based surveys carried out in the west and in Asia have shown that glaucoma remains undetected in nearly 50% of the cases and hence glaucoma related blindness and disability is often underestimated (4-5).

Prompt and effective management of glaucoma is necessary to reduce the incidence of cases of bilateral blindness due to progressive glaucoma. Biological revolution in medicine has provided new avenues for therapeutic intervention. Newer and innovative treatment strategies are being considered for the control of raised intraocular pressure (TOP) by the use of synthetic and herbal drugs in glaucoma.

Presently Available Glaucoma Therapy
  The primary goal in the management of glaucoma is to lower IOP below 20 mm Hg in the patients with mild changes in the optic disc and below 15 mm Hg in the patients with more severe changes. Surgical intervention aiming at increasing the aqueous humor outflow is undertaken when IOP remains uncontrolled even with multiple drug therapy.

The following groups/drugs are widely used in the treatment of glaucoma:

| Group of Drugs | Formulations |
| --- | --- |
| TOPICAL DRUGS | |
| Cholinergic agonists | Pilocarpine, carbechol, physostigmine |
| Adrenergic agonists | Forskolin, isoproterenol, salbutamol, epinephrine |
| Adrenergic antagonists | Timolol, betaxolol, atenolol |
| Prostaglandin analogues | Latanoprost |
| Carbonic anhydrase inhibitors | Trifluoromethazolmide, aminozolamide |
| SYSTEMIC DRUGS | |
| Carbonic anhydrase inhibitor | Acetazolamide, methazolamide, dichlorphenamide |
| Hyper- osmotic agents | Glycerol, mannitol |
| Miscellaneous | Cannabinoids, prostaglandins, ACE inhibitors, melatonin, calcium channel blockers, haloperidol. |

Drawbacks of the Presently Available Treatment
  Synthetic drugs are currently available for the control of intraocular pressure (IOP) but have the drawbacks of being toxic, expensive and often have to be administered multiple times a day resulting in poor patient compliance. Thus, an inexpensive drug with potent ocular hypotensive effect and devoid of side effects with low frequency of application is desirable and its identification will be major achievement for human welfare. Medicinal plant based formulations are being used since long for a variety of diseases. Pilocarpine is one example of antiglaucoma drug of plant origin. A variety of substances of plant origin are known to have antichlolonergic and diuretic activity. Such drugs might be useful antiglaucoma drugs.

Following are the adverse reactions observed for synthetic drugs:

| | Adverse reactions | |
| --- | --- | --- |
| Pharmaceutical agents | Ocular | Systemic |
| Cholinergic agonist Pilocarpine | Stinging, irritation Ciliary spasms (myopia) Miosis (vision) Pupillary block Retinal detachment | Headache, pain Sweating Vomiting/diarrhea Salivation, Bradycardia Arrhythmia Dyspnea |

-continued

| Pharmaceutical agents | Adverse reactions | |
|---|---|---|
| | Ocular | Systemic |
| Adrenergic agonist Epinephrine | Stinging, burning Mydriasis Allergic sensitivity Pigment deposits Cystoid macular edema Increased intraocular pressure (IOP) | Increased blood Pressure Increased heart rate Severe headaches Anxiety |
| Alpha-2 agonists Clonidine | Allergic sensitivity Minimal mydriasis Lid retraction Conjunctival vasoconstriction Stinging, burning Foreign body sensation Hyperemia Conjunctival follicles | Gastrointestinal Discomfort Taste abnormalities Headache Fatigue/drowsiness Oral dryness |
| Topical beta-blockers Timolol Betaxolol | Stinging, burning Superficial punctate keratitis Allergic sensitivity Decreased corneal sensitivity Uveitis 4 | Dyspnea Bronchiole constriction Decreased heart rate Arrhythmias Decreased blood Pressure Depression, confusion Gastrointestinal Discomfort |
| Oral carbonic anhydrase inhibitors Acetazolamide | None | Malaise Depression, confusion Metallic taste Anorexia Diarrhea |
| Topical carbonic anhydrase inhibitors Dorzolamide | Stinging/burning Allergic sensitivity Blurred vision Superficial punctate keratitis Corneal edema | Altered taste |
| Prostaglandin analogs Latanoprost | Blurred vision, Stinging, burning, Hyperemia Foreign body sensation Itching. | Headaches Upper respiratory tract Symptoms |

OBJECTIVES OF THE INVENTION

The object of the present invention is to develop herbal synergistic composition for its IOP lowering and anti glaucoma potential.

Another object of the present invention is to formulate the synergistic herbal composition in to pharmaceutically acceptable ophthalmic dosage form with optimum anti glaucoma activity.

Yet another object of the present invention is to overcome disadvantages associated with commonly used allopathic medicine for glaucoma.

DETAILED DESCRIPTION OF THE INVENTION

Accordingly present invention provides a synergistic herbal composition for lowering IOP in glaucoma comprising synergistically effective amount of extract of herbs selected from *Ocimum* species, *Curcuma* species, *Solanum nigrum* and *Areca catechu* optionally along with a pharmaceutically acceptable excipient or carrier.

In synergistic herbal composition of the present invention, *Ocimum* species is selected from the group consisting of *Ocimum basilicum, Ocimum canum, Ocimum kilimandscaricum, Ocimum sanctum, Ocimum viride* and *Curcuma* species is selected from the group consisting of *Curcuma longa, Curcuma avaleton, Curcuma amada, Curcuma aromatica Salisb.*

A synergistic herbal composition of the present invention comprises:

| S. No. | Herbs | % age by weight |
|---|---|---|
| 1 | Extract of *Ocimum* species | 0.10 to 1.0% |
| 2 | Extract of *Curcuma* species | 0.01 to 0.50% |
| 3 | Extract of *Solanum nigrum* | 0.10 to 0.75% |
| 4 | Extract of *Areca catechu* | 0.10 to 1.0% |

A synergistic herbal composition of the present invention preferably comprises:

| S. No. | Herbs | % age by weight |
|---|---|---|
| 1 | *Ocimum basilicum* extract | 0.50% |
| 2 | *Curcuma longa* extract | 0.10% |
| 3 | *Solanum nigrum* extract | 0.25% |
| 4 | *Areca catechu* extract | 0.25% |

In the preferred embodiment, the synergistic herbal composition of the present invention preferably comprises *Ocimum basilicum, Curcuma longa* and *Solanum nigrum*.

In yet another preferred embodiment, the synergistic herbal composition of the present invention preferably comprises *Ocimum basilicum, Curcuma longa* and *Areca catechu*.

The use of the terms, "synergistic" and "synergistically effective," are used in the present invention to mean a biological effect created from the application of two or more agents to produce a biological effect that is greater than the sum of the biological effects produced by the application of individual agents.

The synergistic herbal composition of the present invention optionally comprising the pharmaceutically acceptable excipients which are selected from the group comprising solubility enhancing agents such as polysorbate, cyclodextrin and their derivative, Cremophore RH 40 and other derivative, Viscosity increasing agents such as Hydroxy propyl methyl cellulose and other suitable cellulose derivative, poly vinyl alcohol, povidone, carbopol caragenin, etc, anti oxidants such as citric acid, EDTA and salts thereof, sodium metabisulphite and other approved water soluble anti oxidants, buffering agents such as citrate, borate, phosphate, citro phosphate and osmolarity adjusting agents such as sodium chloride, mannitol, glycerol, preservatives such as benzalkonium chloride, sorbic acid, methyl paraben, propyl paraben, and salts thereof etc.

The synergistic herbal composition of the present invention is preferably formulated in the form of eye drop, ointment, cream, gel.

The present invention further comprises a process for preparing the said herbal formulation. The process of preparing the said herbal ophthalmic formulation comprises following steps:
  i. Coarsely grinding the individual herb such as herein described and extracting it with solvents having different polarity selected from the group such as water, alcohol, acetone, ethyl acetate, Petroleum ether, chloroform or their mixture in different ratio;
  ii. Optionally concentrating the extract obtained in step (a) under vacuum and converting the same either in the form of thick paste having around 20-30% solids or in the form of dry powder;
  iii. Formulating pharmaceutically acceptable herbal composition by combining the extracts obtained in step (a) or step (b) in different ratios such as herein described to yield the synergistic herbal composition in the form of eye drop, ointment, cream or gel;
  iv. Alternatively the extraction can also be performed using distillation method and distillate can be directly used for formulating synergistic herbal composition such as herein described.

EXPERIMENTAL PROCEDURE

The invention is illustrated by the following examples which are not meant to restrict the scope of the invention in any manner Although the invention has been described with reference to specific embodiments, this description is not meant to be construed in a limiting sense. Various modifications of the disclosed embodiments, as well as alternate embodiments of the invention, will become apparent to persons skilled in the art upon reference to the description of the invention. It is therefore contemplated that such modifications can be made without departing from the spirit or scope of the present invention as defined. In the examples, "part" and "parts" mean "part by weight" and "parts by weight", respectively, unless otherwise specified.

The process for preparing the herbal composition comprises the following steps:
  (i) Extraction of herb: The herbs are cleaned, coarsely ground and extracted with water using 8 times the amount of water by heating it to boil for 10 min. The extract is filtered and concentrated to a thick paste having around 30% of solid content. It is then dried in vacuum drier at a temperature of 60 C or it can also be spray dried or freeze dried. The dried powder is collected, packed after sieving in double poly bag. Alternatively herbs can be distilled and distillate can be used for further formulation development.
  (ii) The extracts as per formula are weighed and dissolved in water containing 0.25% HPMC as viscosity increasing agent under stirring. Additionally Cremophore RH 40 or its suitable derivative is added to increase the solubility.
  (iii) The preparation in centrifuged at about 4000 rpm for 30-60 min to remove the insoluble impurities. Alternatively it can be filtered using what man filter paper.
  (iv) To the clear filtrate suitable preservative (in this case, BKC, methyl and propyl paraben sodium and sorbic acid, phenyl ethyl alcohol and mercury containing preservatives are found to be suitable) are dissolved.
  (v) Disodium EDTA and sodium meta bisulphite as anti oxidants are dissolved in it by stirring
  (vi) Finally pH is adjusted with boric acid/borax, citric acid, sodium citrate, potassium and sodium phosphate to 5-7 and volume is made up with water for injection.
  (vii) The liquid is then filtered using Millipore filter of 0.22 micron and filled in plastic eye drops vial under laminar flow and labeled.
  (viii) The final product is clear, transparent having yellow to yellowish red color having osmolarity of 250-350 mosmol/kg and pH of 5-7.

The anti glaucoma activity of herbal ophthalmic solutions was evaluated in rabbits using following models of glaucoma:
1. Normotensive model: Twelve Albino rabbits of either sex weighing 1.5-2 kg were subjected for baseline IOP measurements using Non Contact Tonometer. The drug (50 ul) was then instilled into one of the eye while the other eye served as the control eye and was instilled with normal saline (50 ul). IOP was then recorded at 30-minute interval for a period of 6 hours.
2. Water loading model: Twelve Albino rabbits of either sex were fasted overnight. The baseline IOP was then recorded next morning and drug (50 ul) was instilled in the test eye and normal saline (50 ul) in control eye. 30 minutes later rabbits were anaesthetized by injecting thiopentone sodium (16 mg/kg BW) in the marginal ear vein. Infant feeding tube was then inserted into the stomach followed by injection of tap water (100 ml/kg) through the tube. IOP was now recorded every 15-min for a period of 120 minutes. The concentration of drug showing best effect in normotensive model was further tested in water loading model. This model mimics the acute glaucomatous attacks.
3. Steroid induced glaucoma model: 12 young rabbits were trained to accept tonometry and then IOP was measured daily for 15 days so as to make a record of baseline TOP. These rabbits were then instilled with prednisolone 1% eye drops (10 ul) in the test eye and normal saline (20 ul) in the control eye, twice a day for a period of 40 days. IOP was measured twice a week during steroid treatment period. At the end of 40 days rabbits were subjected to evaluation of antiglucoma activity. The concentration of drug showing best effect in normotensive model was further tested in steroid induced glaucoma model. TOP measurements were done every 30-minute for a period of 6 hours. This model mimics the chronic open angle glaucoma.

The different ophthalmic formulations were prepared using following formulas:

(i) *Ocimum Basilicum* Ophthalmic Formulation (F1) Comprises:

| S.N. | Ingredients | Quantity for 100 ml (mg) |
| --- | --- | --- |
| 1 | *Ocimum basilicum* extract | 500 |
| 2 | Hydroxy propyl methyl cellulose | 250 |
| 3 | Methyl paraben sodium | 200 |
| 4 | Propyl paraben sodium | 20 |
| 5 | Disodium EDTA | 100 |
| 6 | Sodium metabisulphite | 100 |
| 7 | Boric acid/borax quantity sufficient to pH 6.5 | q.s. |
| 8 | Water for injection q.s. to volume | q.s. |

(ii) *Curcuma longa* Ophthalmic Formulation (F2) Comprises:

| S.N. | Ingredients | Quantity for 100 ml (mg) |
| --- | --- | --- |
| 1 | *Curcuma longa* extract | 100 |
| 2 | Hydroxy propyl methyl cellulose | 250 |
| 3 | Methyl paraben sodium | 200 |
| 4 | Propyl paraben sodium | 20 |
| 5 | Disodium EDTA | 100 |
| 6 | Sodium metabisulphite | 100 |
| 7 | Boric acid/borax quantity sufficient to pH 6.5 | q.s. |
| 8 | Water for injection q.s. to volume | q.s. |

(iii) *Solanum nigrum* Ophthalmic Formulation (F3) Comprises:

| S.N. | Ingredients | Quantity for 100 ml (mg) |
| --- | --- | --- |
| 1 | *Solanum nigrum* extract | 250 |
| 2 | Hydroxy propyl methyl cellulose | 250 |
| 3 | Methyl paraben sodium | 200 |
| 4 | Propyl paraben sodium | 20 |
| 5 | Disodium EDTA | 100 |
| 6 | Sodium metabisulphite | 100 |
| 7 | Boric acid.borax quantity sufficient to pH 6.5 | q.s. |
| 8 | Water for injection q.s. to volume | q.s. |

(iv) *Areca catechu* Ophthalmic Formulation (F4) Comprises:

| S.N. | Ingredients | Quantity for 100 ml (mg) |
| --- | --- | --- |
| 1 | *Areca catechu* extract | 500 |
| 2 | Hydroxy propyl methyl cellulose | 250 |
| 3 | Methyl paraben sodium | 200 |
| 4 | Propyl paraben sodium | 20 |
| 5 | Disodium EDTA | 100 |
| 6 | Sodium metabisulphite | 100 |
| 7 | Boric acid.borax quantity sufficient to pH 6.5 | q.s. |
| 8 | Water for injection q.s. to volume | q.s. |

(v) Combined *Ocimum basilicum, Curcuma Longa, Solanum Nigrum*, ophthalmic formulation (F5) of the present invention comprises:

| S.N. | Ingredients | Quantity for 100 ml (mg) |
| --- | --- | --- |
| 1 | *Ocimum basilicum* extract | 500 |
| 2 | *Curcuma longa* extract | 100 |
| 3 | *Solanum nigrum* extract | 250 |
| 4 | Hydroxy propyl methyl cellulose | 250 |
| 5 | BKC 50% | 20 |
| 6 | Disodium EDTA | 100 |
| 7 | Sodium metabisulphite | 100 |
| 8 | Borax/boric acid quantity sufficient to pH 6.5 | q.s. |
| 9 | Water for injection q.s. to volume | q.s. |

(vi) Combined *Ocimum basilicum, Curcuma Longa, Areca Catechu* Ophthalmic formulation (F6) of the present invention comprises:

| S.N. | Ingredients | Quantity for 100 ml (mg) |
| --- | --- | --- |
| 1 | *Ocimum basilicum* extract | 500 |
| 2 | *Curcuma longa* extract | 100 |
| 3 | *Areca catechu* extract | 500 |
| 4 | Hydroxy propyl methyl cellulose | 250 |
| 5 | Methyl paraben sodium | 200 |
| 6 | Propyl paraben sodium | 20 |
| 7 | Disodium EDTA | 100 |
| 8 | Sodium metabisulphite | 100 |
| 9 | Boric acid/borax quantity sufficient to pH 6.5 | q.s. |
| 10 | Water for injection q.s. to volume | q.s. |

Manufacturing Procedure for Formulation (F1, F2, F3 and F4):
1. Hydroxy propyl methyl cellulose (HPMC) is dissolved in about 50 ml of water under stirring. Once it is dissolved completely, then main active ingredient as per above formula of Formulation (F1, F2, F3 and F4) are added to this and dissolved under stirring.
2. The solution is then centrifuged at 4000 rpm for 30 minutes and clear liquid is collected.
3. Methyl and propyl paraben sodium is dissolved in around 10 ml of water and added to clear filtrate of step 2 under stirring.
4. Item number 5 and 6 are then added and dissolved in main bulk under stirring and pH is checked.
5. pH is then adjusted with dilute borax/boric acid solution and volume is made up.
6. The solution is filtered using 0.22 micron filter aseptically and product is filled in 10 ml three piece plastic vial.

Manufacturing Procedure for Formulation (F5 and F6):
1. Hydroxy propyl methyl cellulose (HPMC) is dissolved in about 50 ml of water under stirring. Once it is dissolved completely, then main active ingredient as per above formula of Formulation (F1, F2, F3 and F4) are added to this and dissolved under stirring.
2. The solution is then centrifuged at 5000 rpm for 30 minutes and clear liquid is collected.
3. methyl and propyl paraben sodium is dissolved in around 10 ml of water and added to clear filtrate of step 2 under stirring.
4. Item number 7 and 8 are then added and dissolved in main bulk under stirring and pH is checked.
5. pH is then adjusted with dilute borax/boric acid solution and volume is made up.
6. The solution is filtered using 0.22 micron filter aseptically and product is filled in 10 ml three piece plastic vial.

TABLE 1

Effect of *Ocimum basilicum* (F1) on normotensive rabbit eye

| Time (Hours) | Test Eye (% Change in IOP) | Control eye (% Change in IOP) | % Difference between test and control eye |
|---|---|---|---|
| 0 | 0 | 0 | 0 |
| 0.5 | −6.08 | 5.92 | −12.00 |
| 1 | −10.12 | 5.79 | −15.92 |
| 1.5 | −12.34 | 3.67 | −16.01 |
| 2 | −17.95 | 4.56 | −22.51 |
| 2.5 | −18.56 | 3.86 | −22.43 |
| 3 | −22.66 | −0.16 | −22.49 |
| 3.5 | −20.64 | −0.43 | −20.22 |
| 4 | −18.47 | 1.56 | −20.03 |
| 4.5 | −13.94 | 1.58 | −15.52 |
| 5 | −12.62 | 3.56 | −16.18 |
| 5.5 | −8.66 | 2.43 | −11.09 |
| 6 | −5.07 | −1.07 | −4.00 |

The IOP reduction in the test eye was −22.61% from baseline at 3 hours post drug instillation and significant effect persisted up to 6 hours post drug instillation (Table 1).

TABLE 2

Effect of *Ocimum basilicum* (F1) in water loading model

| Time (Minutes) | Test eye (% Change in IOP) | Control eye (% Change in IOP) | % Difference between test and control eye |
|---|---|---|---|
| 0 | 0 | 0 | 0 |
| 15 | 23.39 | 54.00 | −30.61 |
| 30 | 50.07 | 80.28 | −30.21 |
| 45 | 66.3 | 99.89 | −33.59 |
| 60 | 63.58 | 95.12 | −31.54 |
| 75 | 40.79 | 68.82 | −28.03 |
| 90 | 24.66 | 52.46 | −27.8 |
| 105 | 10.69 | 27.56 | −16.87 |
| 120 | 4.04 | 17.41 | −13.37 |

The peak IOP rise in test eye was 66.3%, 45 minutes post water loading while the same was 99.89% in control eye. The drug prevented rise in IOP during entire period of experiment with peak effect of −33.59% at 45-minute post water loading (Table 2).

TABLE 3

Effect of *Ocimum basilicum* (F1) in steroid induced model

| Time (Hours) | Test eye (% Change in IOP) | Control eye (% Change in IOP) | % Difference between test and control eye |
|---|---|---|---|
| 0 | 0 | 0 | 0 |
| 0.5 | −9.8093 | −3.56012 | −6.24919 |
| 1 | −18.2329 | −4.49933 | −13.7335 |
| 1.5 | −19.9482 | −5.49952 | −14.4487 |
| 2 | −24.6492 | −5.76607 | −18.8831 |
| 2.5 | −25.3312 | −5.64618 | −19.685 |
| 3 | −26.2759 | −4.99331 | −21.2826 |
| 3.5 | −24.2935 | −4.93426 | −19.3592 |
| 4 | −21.8965 | −4.29147 | −17.605 |
| 4.5 | −17.2735 | −5.72653 | −11.547 |
| 5 | −12.708 | −5.61631 | −7.09164 |
| 5.5 | −10.9236 | −5.17484 | −5.74877 |
| 6 | −9.45058 | −3.86215 | −5.58843 |
| 8 | −1.43136 | −2.09522 | 0.663862 |

The IOP reduction in the test eye was −26.2759% from baseline at 3 hours post drug instillation and significant effect persisted up to 6 hours post drug instillation (Table 3).

TABLE 4

Effect of *Curcuma longa* (F2) on normotensive rabbit eye

| Time (Hours) | Test eye (% Change in IOP) | Control eye (% Change in IOP | % Difference between test and control eye |
|---|---|---|---|
| 0 | 0 | 0 | 0 |
| 0.5 | −18.06 | 2.06 | −20.12 |
| 1 | −24.73 | −2.32 | −22.41 |
| 1.5 | −30.07 | 0.38 | −30.45 |
| 2 | −31.63 | −1.74 | −29.89 |
| 2.5 | −33.70 | −5.51 | −28.19 |
| 3 | −28.13 | −0.41 | −27.72 |
| 3.5 | −28.90 | −0.27 | −28.63 |
| 4 | −23.39 | −0.24 | −23.15 |
| 4.5 | −16.90 | 1.39 | −18.29 |
| 5 | −14.43 | 0.68 | −15.11 |
| 5.5 | −9.61 | −0.39 | −9.23 |
| 6 | −3.07 | 0.01 | −3.09 |

The IOP reduction in the test eye was −33.70% from baseline at 2.5 hours post drug instillation and significant effect persisted up to 6 hours post drug instillation (Table 4).

TABLE 5

Effect of *Curcuma longa* (F2) in water loading model

| Time (Minutes) | Test eye (% Change in IOP) | Control eye (% Change in IOP) | % Difference between test and control eye |
|---|---|---|---|
| 0 | 0 | 0 | 0 |
| 15 | 24.78 | 55.67 | −30.89 |
| 30 | 50.46 | 81.14 | −30.68 |
| 45 | 69.33 | 100.32 | −30.99 |
| 60 | 62.34 | 95.69 | −33.36 |
| 75 | 38.39 | 67.86 | −29.47 |
| 90 | 23.50 | 48.53 | −25.03 |
| 105 | 11.17 | 24.72 | −13.55 |
| 120 | −0.22 | 13.93 | −14.15 |

The peak IOP rise in test eye was 69.33%, 45 minutes post water loading while the same was 100.32% in control eye. The drug prevented rise in IOP during entire period of experiment with peak effect of −33.36% at 60 minute post water loading (Table 5)

TABLE 6

Effect of *Curcuma longa* (F2) in steroid induced model

| Time (Hours) | Test eye (% Change in IOP) | Control eye (% Change in IOP | % Difference between test and control eye |
|---|---|---|---|
| 0 | 0 | 0 | 0 |
| 0.5 | −14.86 | 0 | −14.86 |
| 1 | −22.99 | 0.48 | −23.48 |
| 1.5 | −28.97 | 0.13 | −29.09 |
| 2 | −32.67 | −2.56 | −30.11 |
| 2.5 | −33.01 | −2.81 | −30.20 |
| 3 | −34.34 | −2.81 | −31.54 |
| 3.5 | −30.78 | −2.30 | −28.48 |
| 4 | −26.53 | −1.08 | −25.44 |
| 4.5 | −22.13 | −1.08 | −21.05 |
| 5 | −17.77 | −0.14 | −17.63 |
| 5.5 | −13.77 | −0.14 | −13.63 |
| 6 | −10.74 | −0.14 | −10.59 |
| 8 | −1.82 | −0.92 | −0.90 |

The IOP reduction in the test eye was −34.34% from baseline at 3 hours post drug instillation and significant effect persisted up to 6 hours post drug instillation (Table 6).

TABLE 7

Effect of *Solanum nigrum* (F3) on normotensive rabbit eye

| Time (Hours) | Test eye (% Change in IOP) | Control eye (% Change in IOP | % Difference between test and control eye |
|---|---|---|---|
| 0 | 0 | 0 | 0 |
| 0.5 | −3.62 | 1.56 | −5.18 |

TABLE 7-continued

Effect of *Solanum nigrum* (F3) on normotensive rabbit eye

| Time (Hours) | Test eye (% Change in IOP) | Control eye (% Change in IOP) | % Difference between test and control eye |
|---|---|---|---|
| 1 | −19.61 | −0.63 | −18.97 |
| 1.5 | −22.26 | −0.63 | −21.63 |
| 2 | −23.81 | −0.65 | −23.16 |
| 2.5 | −24.92 | −1.41 | −23.52 |
| 3 | −25.03 | −1.07 | −23.97 |
| 3.5 | −24.69 | −1.42 | −23.27 |
| 4 | −23.31 | −1.75 | −21.56 |
| 4.5 | −18.48 | 0.09 | −18.56 |
| 5 | −15.15 | 0.54 | −15.69 |
| 5.5 | −11.88 | 0.54 | −12.42 |
| 6 | −8.21 | 0.54 | −8.76 |
| 8 | −3.86 | 1.25 | −5.11 |

The IOP reduction in the test eye was −25.03% from baseline at 3 hours post drug instillation and significant effect persisted up to 6 hours post drug instillation (Table 7).

TABLE 8

Effect of *Solanum nigrum* (F3) in water loading model

| Time (Minutes) | Test eye (% Change in IOP) | Control eye (% Change in IOP) | % Difference between test and control eye |
|---|---|---|---|
| 0 | 0 | 0 | 0 |
| 15 | 28.20 | 55.10 | −26.90 |
| 30 | 51.24 | 84.23 | −32.99 |
| 45 | 66.70 | 104.10 | −37.40 |
| 60 | 69.39 | 99.21 | −29.82 |
| 75 | 39.23 | 67.91 | −28.69 |
| 90 | 26.36 | 50.84 | −24.47 |
| 105 | 11.87 | 26.59 | −14.72 |
| 120 | 4.03 | 16.12 | −12.09 |

The peak IOP rise in test eye was 69.39%, 60 minutes post water loading while the same was 104.10% at 45 minute in control eye. The drug prevented rise in IOP during entire period of experiment with peak effect of −37.40% at 45-minute post water loading (table 8).

TABLE 9

Effect of *Solanum nigrum* (F3) in steroid induced model

| Time (Hours) | Test eye (% Change in IOP) | Control eye (% Change in IOP) | % Difference between test and control eye |
|---|---|---|---|
| 0 | 0 | 0 | 0 |
| 0.5 | −11.62 | 1.10 | −12.72 |
| 1 | −31.89 | −1.59 | −30.30 |
| 1.5 | −31.82 | −1.96 | −29.86 |
| 2 | −33.58 | −2.70 | −30.88 |
| 2.5 | −28.52 | −2.84 | −25.68 |
| 3 | −27.39 | −3.76 | −23.64 |
| 3.5 | −25.15 | −3.43 | −21.73 |
| 4 | −25.15 | −3.37 | −21.78 |
| 4.5 | −19.39 | −2.84 | −16.55 |
| 5 | −18.44 | −2.97 | −15.48 |
| 5.5 | −11.25 | 0.80 | −12.05 |
| 6 | −9.00 | 0.80 | −9.80 |
| 8 | −0.26 | 2.29 | −2.55 |

The IOP reduction in the test eye was −33.58% from baseline at 2 hours post drug instillation and significant effect persisted up to 6 hours post drug instillation (Table 9).

TABLE 10

Effect of *areca catechu* (F4) in normotensive model

| Time in hours | Test eye (% Change in IOP) | Control eye (% Change in IOP) | % Difference Treated Eye-Control Eye |
|---|---|---|---|
| 0 | 0.00 | 0.00 | 0.00 |
| 0.5 | −13.59 | −2.54 | −11.05 |
| 1 | −17.63 | −1.16 | −16.47 |
| 1.5 | −19.68 | −1.94 | −17.74 |
| 2 | −20.60 | −0.75 | −19.85 |
| 3 | −17.53 | −2.58 | −14.95 |
| 4 | −15.71 | −1.23 | −14.48 |
| 5 | −9.88 | −0.48 | −9.41 |
| 6 | −5.54 | −2.96 | −2.58 |

The IOP reduction in the test eye was −20.60% from baseline at 2 hours post drug instillation and significant effect persisted up to 6 hours post drug instillation (Table 10).

TABLE 11

Effect of *Areca catechu* (F4) in water loaded model

| Time in minutes | Test eye (% Change in IOP) | Control eye (% Change in IOP) | % Difference Treated Eye-Control eye |
|---|---|---|---|
| 0 | 0.00 | 0.00 | 0.00 |
| 15 | 24.10 | 46.22 | −22.13 |
| 30 | 41.48 | 72.98 | −31.50 |
| 45 | 69.10 | 101.96 | −32.87 |
| 60 | 57.97 | 84.18 | −26.21 |
| 75 | 42.14 | 64.31 | −22.17 |
| 90 | 35.27 | 49.39 | −14.12 |
| 120 | 12.44 | 15.69 | −3.25 |

The peak IOP rise in test eye was 69.10%, 45 minutes post water loading while the same was 101.96% at 45 minute in control eye. The drug prevented rise in IOP during entire period of experiment with peak effect of −32.87% at 45 minute post water loading (Table 11).

TABLE 12

Effect of *areca catechu* (F4) in steroid model

| Time in hours | Test eye (% Change in IOP) | Control eye (% Change in IOP) | % Difference Treated Eye-Control Eye |
|---|---|---|---|
| 0 | 0.00 | 0.00 | 0.00 |
| 0.5 | −10.92 | −0.92 | −10.00 |
| 1 | −16.18 | −0.52 | −15.66 |
| 1.5 | −19.19 | −1.31 | −17.87 |
| 2 | −25.77 | −2.36 | −23.41 |
| 3 | −22.15 | −2.76 | −19.40 |
| 4 | −16.97 | −1.92 | −15.04 |
| 5 | −12.86 | −2.45 | −10.41 |
| 6 | −5.84 | −2.34 | −3.50 |

The IOP reduction in the test eye was −25.77% from baseline at 2 hours post drug instillation and significant effect persisted up to 6 hours post drug instillation (Table 12).

TABLE 13

Effect of *Ocimum basilicum, Curcuma longa, Solanum nigrum* (F5) in normotensive model

| Time (Hours) | Test eye (% Change in IOP) | Control eye (% Change in IOP) | % Difference between test and control eye |
|---|---|---|---|
| 0 | 0 | 0 | 0 |
| 1 | −30.01 | −0.86 | −29.15 |
| 2 | −32.03 | −0.85 | −31.18 |
| 3 | −27.46 | −0.29 | −27.17 |
| 4 | −23.77 | −0.56 | −23.21 |
| 5 | −18.89 | −0.98 | −17.90 |
| 6 | −10.49 | −0.93 | −9.56 |
| 8 | −4.88 | −0.69 | −4.19 |
| 10 | −3.74 | −0.69 | −3.05 |

The IOP reduction in the test eye was −32.03% from baseline at 2 hours post drug instillation and significant effect persisted up to 8 hours post drug instillation (Table 13).

TABLE 14

Comparative data of *curcuma longa*, *Ocimum basilicum* and *Solanum nigrum* (F1, F2, F3) alone and in combination (F5) in normotensive model

| Time (Hours) | % Difference between test and control eye (*S. nigrum*) | % Difference between test and control eye (*O. basilicum*) | % Difference between test and control eye (*C. longa*) | % Difference between test and control eye |
|---|---|---|---|---|
| 0 | 0 | 0 | 0 | 0 |
| 1 | −18.97 | −15.92 | −22.41 | −29.15 |
| 2 | −23.16 | −22.51 | −29.89 | −31.18 |
| 3 | −23.97 | −22.49 | −27.72 | −27.17 |
| 4 | −21.56 | −20.03 | −23.15 | −23.21 |
| 5 | −15.69 | −16.18 | −15.11 | −17.90 |
| 6 | −8.76 | −4.0 | −3.09 | −9.56 |

The maximum peak IOP reduction of −31.18 was observed with instillation of combination of *Ocimum basilicum*, *Curcuma longa* and *Solanum nigrum*, (F5) as compared to individual herbs (Table 14).

TABLE 15

Effect of *Ocimum basilicum*, *Curcuma longa*, *Solanum nigrum* (F5) in water loading model

| Time (Minutes) | Test eye (% Change in IOP) | Control eye (% Change in IOP) | % Difference between test and control eye |
|---|---|---|---|
| 0 | 0 | 0 | 0 |
| 15 | 20.82 | 57.20 | −36.39 |
| 30 | 36.24 | 81.50 | −45.26 |
| 45 | 62.23 | 102.40 | −40.17 |
| 60 | 58.92 | 93.56 | −34.64 |
| 75 | 39.54 | 69.56 | −30.03 |
| 90 | 23.50 | 50.27 | −26.77 |
| 105 | 8.25 | 25.85 | −17.61 |
| 120 | 0.96 | 15.66 | −14.70 |

The peak IOP rise in test eye was 62.23%, 45 minutes post water loading while the same was 102.40% in control eye. The drug prevented rise in IOP during entire period of experiment with peak effect of −45.26% at 30 minute post water loading (Table 15).

TABLE 16

Comparative data of *Ocimum basilicum*, *Curcuma longa*, *Solanum nigrum* alone and in combination in water loading model.

| Time (Minutes) | % Difference between test and control eye (*Solanum nigrum*) | % Difference between test and control eye (*O. basilicum*) | % Difference between test and control eye (*C. longa*) | % Difference between test and control eye (combination) |
|---|---|---|---|---|
| 0 | 0 | 0 | 0 | 0 |
| 15 | −26.90 | −30.61 | −30.89 | −36.39 |
| 30 | −32.99 | −30.21 | −30.68 | −45.26 |
| 45 | −37.40 | −33.59 | −30.99 | −40.17 |
| 60 | −29.82 | −31.54 | −33.36 | −34.64 |
| 75 | −28.69 | −28.03 | −29.47 | −30.03 |
| 90 | −24.47 | −27.8 | −25.03 | −26.77 |
| 105 | −14.72 | −16.87 | −13.55 | −17.61 |
| 120 | −12.09 | −13.37 | −14.15 | −14.70 |

The maximum protection against the rise in IOP with a difference of −45.26% between test and control eyes was observed with F5 instillation at 30 minutes post water loading as compared to individual herbs (Table 16).

TABLE 17

Effect of *Ocimum basilicum*, *Curcuma longa*, *Solanum nigrum* (F5) in steroid induced model

| Time (Hours) | Test eye (% Change in IOP) | Control eye (% Change in IOP) | % Difference between test and control eye |
|---|---|---|---|
| 0 | 0 | 0 | 0 |
| 1 | −38.37 | −0.86 | −37.51 |
| 2 | −42.18 | −0.85 | −41.33 |
| 3 | −39.25 | −0.29 | −38.96 |
| 4 | −31.69 | −0.56 | −31.13 |
| 5 | −24.14 | −0.98 | −23.16 |
| 6 | −16.27 | −0.93 | −15.34 |
| 8 | −14.19 | −0.69 | −13.50 |
| 10 | −9.20 | −0.69 | −8.51 |

The IOP reduction in the test eye was −42.18% from baseline at 2 hours post drug instillation and significant effect persisted up to 10 hours post drug instillation (Table 17).

TABLE 18

Comparative data of *curcuma longa*, *Ocimum basilicum* and *Solanum nigrum* alone and in combination in Steroid model.

| Time (Hours) | % Difference between test and control eye (*S. nigrum*) | % Difference between test and control eye (*O. basilicum*) | % Difference between test and control eye (*C. longa*) | % Difference between test and control eye (Combination) |
|---|---|---|---|---|
| 0 | 0 | 0 | 0 | 0 |
| 1 | −30.30 | −13.73 | −23.48 | −37.51 |
| 2 | −30.88 | −18.88 | −30.11 | −41.33 |
| 3 | −23.64 | −21.28 | −31.54 | −38.96 |
| 4 | −21.78 | −17.60 | −25.44 | −31.13 |
| 5 | −15.48 | −7.09 | −17.63 | −23.16 |
| 6 | −9.80 | −5.56 | −10.59 | −15.34 |

The maximum peak IOP reduction of −41.33 was observed with instillation of combination of *Ocimum basilicum*, *Curcuma longa* and *Solanum nigrum*, (F5) as compared to individual herbs (Table 18).

TABLE 19

Effect of *Ocimum basilicum*, *Curcuma longa*, *Areca catechu* (F6) in normotensive model

| Time (Hours) | Test eye (% Change in IOP) | Control eye (% Change in IOP) | % Difference between test and control eye |
|---|---|---|---|
| 0 | 0 | 0 | 0 |
| 1 | −26.38 | −1.60 | −24.78 |
| 2 | −32.58 | −2.12 | −30.46 |
| 3 | −31.51 | −3.16 | −28.36 |
| 4 | −27.54 | −2.85 | −24.70 |
| 5 | −20.01 | −2.15 | −17.87 |
| 6 | −13.95 | −1.01 | −12.95 |
| 7 | −10.35 | −1.79 | −8.56 |
| 8 | −7.86 | −2.13 | −5.73 |
| 10 | −3.48 | −1.40 | −2.07 |

The IOP reduction in the test eye was −32.58% from baseline at 2 hours post drug instillation and significant effect persisted up to 8 hours post drug instillation (Table 19).

TABLE 20

Comparative data of *curcuma longa*, *Ocimum basilicum* and *Areca catechu* alone and in combination in Normotensive model.

| Time (Hours) | % Difference between test and control eye (*A. catechu*) | % Difference between test and control eye (*O. basilicum*) | % Difference between test and control eye (*C. longa*) | % Difference between test and control eye (combination) |
|---|---|---|---|---|
| 0 | 0 | 0 | 0 | 0 |
| 1 | −16.47 | −15.92 | −22.41 | −24.78 |
| 2 | −19.85 | −22.51 | −29.89 | −30.46 |
| 3 | −14.95 | −22.49 | −27.72 | −28.36 |
| 4 | −14.48 | −20.03 | −23.15 | −24.70 |
| 5 | −9.41 | −16.18 | −15.11 | −17.87 |
| 6 | −2.58 | −4.0 | −3.09 | −12.95 |

The maximum peak IOP reduction of −30.46 was observed with instillation of combination of *Ocimum basilicum*, *Curcuma longa* and *Areca catechu* (F6) as compared to individual herbs (Table 20).

TABLE 21

Effect of *Ocimum basilicum*, *Curcuma longa*, *Areca catechu* (F6) in water loading model

| Time (Minutes) | Test eye (% Change in IOP) | Control eye (% Change in IOP) | % Difference between test and control eye |
|---|---|---|---|
| 0 | 0 | 0 | 0 |
| 15 | 24.69 | 57.06 | −32.37 |
| 30 | 36.29 | 77.04 | −40.75 |
| 45 | 57.48 | 103.99 | −46.51 |
| 60 | 57.90 | 93.78 | −35.89 |
| 75 | 45.19 | 75.29 | −30.10 |
| 90 | 27.11 | 53.11 | −26.01 |
| 120 | 7.07 | 27.43 | −20.35 |

The peak IOP rise in test eye was 57.90%, 60 minutes post water loading while the same was 103.99% at 45 minute in control eye. The drug prevented rise in IOP during entire period of experiment with peak effect of −46.51% at 45 minute post water loading (Table 21).

TABLE 22

Comparative data of *Ocimum basilicum*, *Curcuma longa*, *Areca catechu* alone and in combination in water loading model

| Time (Minutes) | % Difference between test and control eye (*Areca catechu*) | % Difference between test and control eye (*O. basilicum*) | % Difference between test and control eye (*C. longa*) | % Difference between test and control eye (combination) |
|---|---|---|---|---|
| 0 | 0 | 0 | 0 | 0 |
| 15 | −22.13 | −30.61 | −30.89 | −32.37 |
| 30 | −31.50 | −30.21 | −30.68 | −40.75 |
| 45 | −32.87 | −33.59 | −30.99 | −46.51 |
| 60 | −26.21 | −31.54 | −33.36 | −35.89 |
| 75 | −22.17 | −28.03 | −29.47 | −30.10 |
| 90 | −14.12 | −27.8 | −25.03 | −26.01 |
| 120 | −3.25 | −16.87 | −13.55 | −20.35 |

The maximum protection against the rise in IOP with a difference of −46.51% between test and control eyes was observed with F6 instillation at 45 minutes post water loading as compared to individual herbs (Table 22).

TABLE 23

Effect of *Ocimum basilicum*, *Curcuma longa*, *Areca catechu* (F6) in steroid induced model

| Time (Hours) | Test eye (% Change in IOP) | Control eye (% Change in IOP) | % Difference between test and control eye |
|---|---|---|---|
| 0 | 0 | 0 | 0 |
| 1 | −38.37 | −0.86 | −20.00 |
| 2 | −42.18 | −0.85 | −34.2 |
| 3 | −39.25 | −0.29 | −28.7 |
| 4 | −31.69 | −0.56 | −27.00 |
| 5 | −24.14 | −0.98 | −20.5 |
| 6 | −16.27 | −0.93 | −16.6 |
| 8 | −14.19 | −0.69 | −8.3 |
| 10 | −9.20 | −0.69 | −5.2 |

The IOP reduction in the test eye was −42.18% from baseline at 2 hours post drug instillation and significant effect persisted up to 10 hours post drug instillation (Table 23).

TABLE 24

Comparative data of *curcuma longa*(F2), *Ocimum basilicum*(F1) and *Areca catechu* (F4) alone and in combination(F6) in Steroid model.

| Time (Hours) | % Difference between test and control eye (*A. catechu*) | % Difference between test and control eye (*O. basilicum*) | % Difference between test and control eye (*C. longa*) | % Difference between test and control eye (Combination) |
|---|---|---|---|---|
| 0 | 0 | 0 | 0 | 0 |
| 1 | −15.66 | −13.7 | −23.48 | −20.00 |
| 2 | −23.41 | −18.88 | −30.11 | −34.2 |
| 3 | −19.40 | −21.28 | −31.54 | −28.7 |
| 4 | −15.04 | −17.60 | −25.44 | −27.00 |
| 5 | −10.41 | −7.09 | −17.63 | −20.5 |
| 6 | −3.50 | −5.59 | −10.59 | −16.6 |

The maximum peak IOP reduction of −34.20 was observed with instillation of combination of *Ocimum basilicum*, *Curcuma longa* and *Areca catechu* (F6) as compared to individual herbs (Table 24).

Results:

From the above results, surprisingly the herbal composition of the present invention comprising synergistic effective amount of *Solanum nigrum*, *Curcuma longa*, *Ocimum basilicum* (Formulation-F5) and *Curcuma longa*, *Ocimum basilicum*, *Areca catechu* (Formulation-F6) showed enhanced and surprising effects as compared to the individual formulations (F1, F2, F3 and F4). Therefore the said herbal composition (F5 and F6) are working synergistically.

Example 1

For Formulating the Ophthalmic Drops

| S.N. | Ingredients | Quantity per 100 ml |
|---|---|---|
| 1 | *Solanum nigrum* extract | 250 mg |
| 2 | *Ocimum basilicum* extract | 500 mg |
| 3 | *Curcuma longa* extract | 100 mg |
| 4 | Hydroxy propyl methyl cellulose | 250 mg |
| 5 | Cremophore RH 40 | 1000 mg |
| 6 | Methyl paraben sodium | 200 mg |
| 7 | Propyl paraben sodium | 20 mg |
| 8 | Disodium EDTA | 100 mg |
| 9 | Sodium metabisulphite | 100 mg |

-continued

| S.N. | Ingredients | Quantity per 100 ml |
|---|---|---|
| 10 | Citric acid | 350 mg |
| 11 | Disodium hydrogen phosphate | 900 mg |
| 12 | Sodium chloride | 170 mg |
| 13 | Water for injection | q.s. |

Manufacturing Procedure:
1. Hydroxy propyl methyl cellulose (HPMC) is dissolved in about 50 ml of water under stirring. Cremophore RH 40 is added to this solution and dissolved under stirring. Once it is dissolved completely, then main active ingredient as per above formula (S. No. 1-3) are added to this and dissolved under stirring.
2. The solution is then centrifuged at 5000 rpm for 30 minutes and clear liquid is collected.
3. Methyl and propyl paraben sodium is dissolved in around 10 ml of water and added to clear filtrate of step 2 under stirring.
4. Item number 8 and 9 are then added and dissolved in main bulk under stirring and pH is checked.
5. Finally citric acid and sodium phosphate are added to bulk and volume is made up.
6. The solution is filtered using 0.22 micron filter aseptically and product is filled in 10 ml three piece plastic vial.

Example 2

For Formulating the Gel

| S.N. | Ingredients | Quantity per 100 ml |
|---|---|---|
| 1 | *Solanum nigrum* extract | 250 mg |
| 2 | *Ocimum basilicum* extract | 500 mg |
| 3 | *Curcuma longa* extract | 100 mg |
| 4 | Hydroxy propyl methyl cellulose | 250 mg |
| 5 | Cremophore RH 40 | 1000 mg |
| 6 | Methyl paraben sodium | 200 mg |
| 7 | Propyl paraben sodium | 20 mg |
| 8 | Carbomer 971P | 150 mg |
| 9 | Sodium hydroxide | q.s. |
| 10 | Disodium EDTA | 100 mg |
| 11 | Sodium metabisulphite | 100 mg |
| 12 | Citric acid | 350 mg |
| 13 | Disodium hydrogen phosphate | 900 mg |
| 14 | Sodium chloride | 170 mg |
| 15 | Water for injection | q.s. |

1. Hydroxy propyl methyl cellulose (HPMC) is dissolved in about 50 ml of water under stirring. Cremophore RH 40 is added to this solution and dissolved under stirring. Once it is dissolved completely, then main active ingredient as per above formula (S. No. 1-3) are added to this and dissolved under stirring.
2. The solution is then centrifuged at 5000 rpm for 30 minutes and clear liquid is collected.
3. Methyl and propyl paraben sodium is dissolved in around 10 ml of water and added to clear filtrate of step 2 under stirring.
4. Item number 8 is added under slow stirring, once it is dissolved then pH is increased to about 6.5 with dilute sodium hydroxide solution. Item No. 10 and 11 are then added and dissolved in main bulk under stirring and pH is checked.
5. Finally citric acid and sodium phosphate are added to bulk and volume is made up.
6. The solution is filtered using 0.22 micron filter aseptically and product is filled in 10 ml three piece plastic vial.

We claim:
1. An herbal ophthalmic composition for lowering intraocular pressure comprising:
  (i) an *Ocimum* species extract, in an amount of 0.1 to 1.0% by weight;
  (ii) a *Curcuma* species extract, in an amount of 0.01 to 0.5% by weight; and
  (iii) one or both of a *Solanum nigrum* extract, in an amount of 0.1 to 0.75% by weight, and an *Areca catechu* extract, in an amount of 0.1 to 1.0% by weight;
  wherein the composition optionally comprises one or more pharmaceutically acceptable excipients and/or carriers, and wherein the composition is effective in lowering intraocular pressure in a subject having glaucoma.

2. The herbal ophthalmic composition as claimed in claim 1, wherein the *Ocimum* species is selected from the group consisting of *Ocimum basilicum, Ocimum canum, Ocimum kilimandscaricum, Ocimum sanctum, Ocimum viride* and the *Curcuma* species is selected from the group consisting of *Curcuma longa, Curcumavaleton, Curcuma amad, Curcuma aromatica Salisb.*

3. The herbal ophthalmic composition as claimed in claim 1, wherein the amount of the *Ocimum* species extract is in an amount of 0.50% by weight; the amount of the *Curcuma* species extract is in an amount of 0.1% by weight; the amount of the *Solanum nigrum* extract is in an amount of 0.25% by weight; and the amount of the *Areca catechu* extract is in an amount of 0.25% by weight.

4. The herbal ophthalmic composition as claimed in claim 1 or 2, wherein the composition comprises *Ocimum basilicum* extract, *Curcuma longa* extract and *Solanum nigrum* extract.

5. The herbal ophthalmic composition as claimed in claim 1 or 2, wherein the composition comprises *Ocimum basilicum, Curcuma longa* and *Areca catechu*.

6. The herbal ophthalmic composition as claimed in claim 1, wherein the pharmaceutically acceptable excipients are selected from the group consisting of a solubility enhancing agent, a viscosity increasing agent, an antioxidant, a buffering agent, an osmolarity adjusting agent and a preservative.

7. The herbal ophthalmic composition as claimed in claim 1, wherein the composition is in the form of an eye drop, ointment, cream or gel.

8. The herbal ophthalmic composition of claim 6, wherein the solubility enhancing agent is polysorbate, cyclodextrin, a cyclodextrin derivative or Cremophore RH 40.

9. The herbal ophthalmic composition of claim 6, wherein the viscosity increasing agent is hydroxypropylmethylcellulose, a cellulose derivative, polyvinyl alcohol, povidone, carbopol or carageenin.

10. The herbal ophthalmic composition of claim 6, wherein the antioxidant is citric acid, EDTA, a salt of EDTA or sodium metabisulphite.

11. The herbal ophthalmic composition of claim 6, wherein the buffering agent is citrate, borate, phosphate or citro phosphate.

12. The herbal ophthalmic composition of claim 6, wherein the osmolarity adjusting agent is sodium chloride, mannitol or glycerol.

13. The herbal ophthalmic composition of claim 6, wherein the preservative is benzalkonium chloride or a salt thereof, sorbic acid or a salt thereof, methyl paraben or a salt thereof or propyl paraben or a salt thereof.

14. The herbal ophthalmic composition as claimed in claim 1, wherein the composition comprises *Ocimum basilicum* extract in an amount of 0.50% by weight, *Curcuma longa* extract in an amount of 0.1% by weight, *Solanum nigrum* extract in an amount of 0.25% by weight and *Areca catechu* extract in an amount of 0.25% by weight.

15. The herbal ophthalmic composition as claimed in claim 1, wherein the composition comprises *Ocimum basilicum* extract in an amount of 0.50% by weight, *Curcuma longa* in an amount of 0.1% by weight and *Solanum nigrum* extract in an amount of 0.25% by weight.

16. The herbal ophthalmic composition as claimed in claim 1, wherein the composition comprises *Ocimum basilicum* extract in an amount of 0.50% by weight, *Curcuma longa* in an amount of 0.1% by weight and *Areca catechu* extract in an amount of 0.5% by weight.

17. A process for preparing the herbal ophthalmic composition as claimed in claim 1 comprising:
   (i) coarsely grinding each of the herbs and extracting each of the ground herbs with a solvent selected from the group consisting of water, alcohol, acetone, ethyl acetate, petroleum ether, chloroform, and mixtures thereof;
   (ii) optionally concentrating each of the extracts obtained in step (i) under vacuum, and forming each of the concentrated extracts into a paste or a dry powder; and
   (iii) combining effective amounts of the paste and/or dry powder of each extract to obtain a mixture, and formulating the mixture into an eye drop, ointment, cream, or gel, wherein the eye drop, ointment, cream, or gel formulation is the herbal ophthalmic composition.

* * * * *